United States Patent [19]
Sullivan et al.

[11] 4,182,750
[45] Jan. 8, 1980

[54] BLOODCOMPATIBLE FUNCTIONAL POLYMERS

[76] Inventors: Thomas E. Sullivan, 9308 Belmart Rd., Potomac, Md. 20854; Oscar L. Wright, 11 Kathy La., Monroe, La. 71203

[21] Appl. No.: 789,498

[22] Filed: Apr. 21, 1977

[51] Int. Cl.$^2$ ............... A61K 29/00; A61K 43/00
[52] U.S. Cl. ......................... 424/1; 128/1.1; 128/214 R; 210/321 B; 422/44; 424/1.5; 424/9
[58] Field of Search ............... 424/1, 1.5, 12, 9; 210/321 B; 260/112 R; 23/258.5 A; 128/1.1, 214 R; 422/44

[56] References Cited

U.S. PATENT DOCUMENTS

| | | | |
|---|---|---|---|
| 3,434,467 | 3/1969 | Anderson et al. | 128/1.1 |
| 3,514,438 | 5/1970 | Bixler et al. | 23/258.5 A |
| 3,673,612 | 7/1972 | Merrill et al. | 23/258.5 A |
| 3,853,987 | 12/1974 | Dreyer | 424/1 |
| 3,938,953 | 2/1976 | Paschalis et al. | 424/1 |
| 3,959,079 | 5/1976 | Mareschi et al. | 260/112 R |
| 3,995,019 | 11/1976 | Jerome | 424/12 |
| 4,008,047 | 2/1977 | Peterson | 210/321 B |
| 4,010,250 | 3/1977 | Parikh et al. | 424/1 |
| 4,012,317 | 3/1977 | Kuntz et al. | 210/321 B |
| 4,031,201 | 6/1977 | Lostia et al. | 424/12 |

Primary Examiner—Benjamin R. Padgett
Assistant Examiner—Christine M. Nucker

[57] ABSTRACT

High molecular weight polymeric materials, which have incorporated within their structure modified protein(s), carbohydrate(s), nucleic acid(s), and/or lipid(s), capable of either transferring to blood, other biological fluid(s) or tissue(s), a desired substance(s), such as, for example, oxygen, selected antibody(ies), trace element(s), radioactively tagged structure(s), nutrient(s), enzyme(s), and/or other organic or inorganic chemical(s), drug(s) and pharmaceutical(s) of therapeutic value, or of extracting from blood, other biological fluid(s) or tissue(s), an undesired substance(s), such as, for example, carbon dioxide, toxic metabolic product(s), drug(s), and/or other organic or inorganic chemical(s), element(s), or deleterious substance(s). These polymeric materials are compatible with blood, other biological fluid(s) and tissue(s). They may be modified or combined so that the transfer of desired substance(s) to the blood, biological fluid(s) or tissue(s) can be carried out either simultaneous with, prior to, or subsequent to the extraction of undesirable substance(s) from blood, biological fluid(s) or tissue(s).

14 Claims, No Drawings

BLOODCOMPATIBLE FUNCTIONAL POLYMERS

BACKGROUND OF THE INVENTION

The present invention relates to a series of polymeric materials with medically oriented properties. More particularly, the present invention relates to a series of polymeric materials for medical use in the modification of blood, other biological fluid(s), or tissue(s) whereby specific desirable substances can be added to the blood, biological fluid(s), or tissue(s) and/or specific undesirable material(s) removed from the blood, fluid or tissue.

In the prior art there are a number of devices and techniques used for the modification of human blood. There are simple metabolic means that have been used for centuries, wherein a person's diet is augmented or supplemented with, for example, specific foods, drugs or vitamin enriching materials, and the desired blood modifying substances are introduced into the blood stream through the normal physiological functions of the body. Parenteral injection of materials for blood modification is a common practice. For almost a quarter of a century mechanical devices that employ thin film techniques, generally through bloodwetted screens, have been used to contact blood with an air stream to remove carbon dioxide from the blood and add oxygen to the blood, and these are the devices currently used as "artificial lungs" in open heart and lung by-pass surgery.

More recently, a number of mechanical devices have been developed for use in removing from human blood and other biological fluids certain metabolic waste products unable to be handled by diseased or damaged kidneys, and these, in general, employ the process of dialysis across specially designed membranes.

Of still more recent origin is the practice of treating patients suffering from kidney failure, liver malfunction, or poisoning by pumping the patient's blood through a column of specially prepared activated charcoal or special resin, removing the deleterious or toxic materials by surface adsorption in a technique known as hemoperfusion.

The materials comprising the current invention are not intended to supplant such well-established techniques for blood modification as diet substitutions, oral medication or direct injection, but they are to be used as replacements for thin film blood aerators and as improvements on or adjuncts to activated charcoal or resin hemoperfusion columns. Furthermore, incorporation of these materials in the membranes of renal dialysis machines will substantially improve the efficacy of dialysis treatments.

The mechanical type blood oxygenators currently being used generally consist of an upper reservoir from which blood flows by gravity into some form of distributing trough before flowing downward in thin films on rectangular or cylindrical screens alongside which air is blown in an upward stream, thereby giving a countercurrent contact of air and blood. This permits the oxygen from the air to replenish the hemoglobin of the blood with oxygen. Simulataneously it allows the carbon dixoide being carried by the amino acid portion of the hemoglobin molecule to be released to the air. This counterflow of oxygen and carbon dioxide between hemoglobin and air is due primarily to the difference in partial pressures of oxygen and carbon dioxide in the blood and in the air. The respirated blood, after flowing down over the screen or screens is collected in a second reservoir at the bottom of the apparatus where it is then picked up by a pump and returned to the body's vascular system. In open heart surgery, two pumps are required to maintain the blood flow, one to carry the flow to the upper reservoir of the blood aerator, and one to carry the blood from the lower reservoir back to the patient. In lung by-pass operations, only one pump is necessary. Oxygenators currently in use require a volume of approximately two liters of blood as an initial charge, and this normally requires donor blood, since the average human circulatory system only has a capacity of about five and one-half liters of blood. This usage of donor blood increases the danger of contaminating the patient's blood with unknown and possibly undeterminable deleterious factors, even though every precaution is taken to get a "perfect" blood match.

Advantages of using the polymeric materials comprising this invention as blood oxygenators and removers of carbon dioxide rather than mechanical devices of the type just described are: (1) the possibility of damaging blood components through mechanical attrition is reduced, since no pump, or at most a single pump, is required; (2) donor blood is generally not required inasmuch as the priming volume in the column of polymeric material is sufficiently small to permit charging with the patient's own blood, thus eliminating the danger of possible contamination or reaction from donor blood; and, (3) for patients requiring other than simple blood respiration, it is very easy for additional prescribed substances to be added to or withdrawn from the patient's blood through the incorporation of more than one functional polymer in the polymer treatment column.

In dialysis treatment of biological fluids of patients with kidney and liver malfunction and/or poisoning, the materials comprising this invention can easily and advantageously be added to or incorporated on or within the dialysis membrane or other materials, thereby providing chemical means in addition to dialysis for removal of undesirable constituents from the patient's biological fluids. In these cases, the functional polymers would be adjuncts to rather than substitutes for dialysis treatment.

The newly developed technique of hemoperfusion constitutes an area wherein the polymeric materials covered by this invention can be substituted for or added to currently used adsorbents with considerable advantage. The current treatment removes toxins through the process of surface adsorption, whereas specially synthesized polymers described in this invention remove toxic or unwanted materials through the process of chemisorption, a much more efficient technique per available surface area since it is essentially thermodynamically irreversible. By proper combinations of different specifically synthesized polymeric materials in a treatment column or columns, additions or deletions can be made to the patient's blood simultaneous with the removal of the toxins, thereby providing for additional therapeutic factors. Chemisorbents such as those described in this invention, can also be combined with or used in conjunction with plasmaphoresis, or other centrifugation methods, for separating and treating biological fluids.

Materials such as those described in this invention can be used to remove toxins or unwanted substances from body areas or cavities, and/or modifications of these materials can be used to administer antibody(ies), trace element(s), radioactively tagged structure(s), nutrient(s), enzyme(s) and/or other organic or inorganic chemical(s), drug(s) or pharmaceutical(s), to these same body areas or cavities. Typical treatment sites are: skin through topical application; subcutaneous or other tissue by injection or surgical implant; gastrointestinal tract through oral ingestion, surgical implant or colonic infusion; nasopharyngeal region by application or surgical implant; genitourinary tract by infusion or surgical implant; and/or any other body area or cavity through suitable means.

These and other objectives and advantages of the present invention will be apparent from the following description.

SUMMARY OF THE INVENTION

Briefly, in accordance with the present invention, high molecular weight polymeric materials are made available for use in the medical treatment of blood, other biological fluid(s) or tissue(s). These materials, which are compatible with blood, other biological fluid(s) or tissue(s), have incorporated within their structures proteins, carbohydrates, nucleic acids, and/or lipids, specifically chosen and modified so that, when these materials are contacted with blood, biological fluid(s), or tissue(s), they provide the means whereby desired substances can be added to blood, fluid or tissue and/or undesired substances removed from blood, fluid or tissue.

DETAILED DESCRIPTION OF THE INVENTION

The materials comprising this invention are high molecular weight polymers, modified for use in the medical treatment of blood, biological fluid(s), or tissue(s), in order to produce, either directly or indirectly, certain specific therapeutic effects upon the patient or animal whose blood or biological fluid or tissue is being treated. These modified polymers are produced by the addition of amino acids, carbohydrates, nucleic acids, and/or lipids, either singly or as chains or rings, to a base polymer. The base polymer is formed by the vinyl polymerization of styrene, vinyl chloride, maleic anhydride, acrylic acid derivatives, or nitrilo substituted ethylenes, either singly or as copolymers. For example, polystyrene is a material having aromatic rings attached to every other carbon atom in a linked chain of from one hundred to one thousand carbon atoms. Each of these aromatic rings is a site available for the addition, by appropriate chemical synthesis, of an amino acid, carbohydrate, nucleic acid, or lipid selected for its specific chemical structure. The length of the added chain or the ring size can be readily controlled. For example, in the case of an amino acid chain, additional amino acid groups, of the same or of different chemical structure, can be added to the first amino acid through normal peptide linkage, and this process is continued until the final amino acid (protein) chain is of the length desired to give to the finished material its desired functional properites.

As a more specific example, if a material is desired for use in oxygenating blood and in simultaneously removing carbon dioxide from blood, the amino acid would be either identical to or very similar to that in globin, the protein chain to which heme is bound to give hemoglobin. Heme would then be attached to the protein chains to give a high molecular weight polymeric material with chemical properties substantially identical to hemoglobin. In using this material, it would first be aerated in order to provide for oxygen combination with the heme units, after which it would be available for use as an "artificial lung" material. When this oxygenated material is then brought into contact with blood flowing from a patient through a column of the material, the oxygen on the heme of the material transfers, because of the difference in unit concentration, to the somewhat depleted heme of the hemoglobin in the blood, and this process continues until an oxygen equilibrium between the material and the blood is approached. Simultaneous with this oxygen transfer is the transport of carbon dioxide from the globin of the blood's hemoglobin to the protein chain of the material, since the amino acids in the chain act as weak base sites for ready combination with the carbon dioxide, and this carbon dioxide transfer also continues until equilibrium is approached.

In a similar fashion, high molecular weight polymeric materials are synthesized with specific chemical properties so that they can either readily combine with chemicals that are to be removed from blood, biological fluid(s) or tissue(s), and/or easily transfer desired chemicals to the blood, biological fluid(s) or tissue(s). These materials may be used in native form, or they may be coated with other biocompatible polymers in order to improve the fluid mechanical properties and/or the hemocompatibility of these materials, thereby increasing the efficacy of these materials in removing toxins or unwanted substances from blood, biological fluid(s) or tissue(s). Furthermore, the materials in coated form may be used to delay or improve the release of specific substances to blood, biological fluid(s) or tissue(s).

The specific structures and variations of one of these materials have been described herein for purposes of illustration only, and it is to be understood that various modifications, combinations and equivalents of such structures will be apparent to one skilled in the art. Accordingly, the present invention includes such modifications, combinations, and equivalents, and is to be limited only in accordance with the appended claims.

We claim:

1. Therapeutic materials made by chemically bonding to a base polymer formed by the vinyl polymerization of styrene, vinyl chloride, maleic anhydride, acrylic acid derivatives or nitrilo substituted ethylene, at least one substance selected from the group consisting of a modified protein, a carbohydrate, a nucleic acid, and a lipid, said substance being capable of transferring a desired ingredient to blood, biological fluid or tissue, upon contact therewith, these therapeutic materials being compatible with blood, biological fluid and tissue, and producing no undesirable effects.

2. A material in accordance with claim 1 which can oxygenate blood when blood is passed through and over these materials.

3. A material in accordance with claim 1 which can remove carbon dioxide from blood when blood is passed through and over these materials.

4. A material in accordance with claim 1 which oxygenates blood or biological fluid while simultaneously removing carbon dioxide from the same blood of fluid.

5. A material in accordance with claim 1 which adds to blood, biological fluid or tissue measured doses of either an antibody, a trace element, a radioactively tagged structure, a nutrient, an enzyme, or other organic or inorganic chemical drug or pharmaceutical of a therapeutic nature.

6. A material in accordance with claim 1 which extracts from blood, biological fluid or tissue, toxic metabolic products, toxic materials of other than metabolic origin, drugs, and other chemicals, elements, or substance deleterious to the host body.

7. A material in accordance with claim 1 designed to simultaneously transfer beneficial substances to blood, biological fluid or tissue and remove deleterious substances from the same blood, fluid, or tissue.

8. A material in accordance with claim 1 which is used in conjunction with dialysis membranes and other adsorbent materials to improve the efficiency of removing unwanted toxins or deleterious substances in the dialysis or sorbent treatment of patients with kidney malfunction, liver malfunction, or poisoning.

9. A material in accordance with claim 6 which is incorporated within the physical or chemical structure of dialysis membrane materials.

10. A method for the adjunctive treatment of body fluids or dialysate during peritoneal dialysis which comprises treating said body fluids or dialysate with a material as set forth in claim 1.

11. A method for enterally or parenterally removing toxins and unwanted substances from body areas or cavities or for administering to body areas or cavities an antibody, a trace element, a radioactively tagged structure, a nutrient, an enzyme, or other organic or inorganic chemical, drug, or pharmaceutical which comprises introducing into said body areas or cavities a material as set forth in claim 1.

12. A method for removing toxins and unwanted substances from blood, biological fluid or tissue or for administering to blood, biological fluid or tissue an antibody, a trace element, a radioactively tagged structure, a nutrient, an enzyme or other organic or inorganic chemical, drug, or a pharmaceutical which comprises introducing into said blood, fluid or tissue a material as set forth in claim 1.

13. A method for removing unwanted substances from or adding prescribed substances to fractions of blood or biological fluid obtained by plasmaphoresis or centrifugation methods which comprises adding to said fractions of blood or biological fluid a material as set forth in claim 1.

14. A method for removing toxins or unwanted substances from blood, biological fluid or tissue or to delay or improve the release of specific substances to blood, biological fluid or tissues which comprises encapsulating the material set forth in claim 1 with any of a number of clinically proven encapsulating substances and introducing said encapsulated material to said blood, biological fluid or tissue.

* * * * *